United States Patent [19]

Lednicer

[11] 4,115,589
[45] Sep. 19, 1978

[54] COMPOUNDS, COMPOSITIONS AND METHOD OF USE

[75] Inventor: Daniel Lednicer, Evansville, Ind.

[73] Assignee: The Upjohn Company, Kalamazoo, Mich.

[21] Appl. No.: 797,782

[22] Filed: May 17, 1977

[51] Int. Cl.² .......................... A01N 9/20; C07C 91/02
[52] U.S. Cl. .............................. 424/330; 260/340.9 R; 260/464; 260/501.18; 260/501.19; 260/570.5 CA; 424/305; 424/316; 560/173

[58] Field of Search ................ 260/570.5 CA, 501.18, 260/501.19; 424/316, 330

[56]  References Cited
U.S. PATENT DOCUMENTS 4,065,573   12/1977   Lednicer ....................... 260/570.5 X

*Primary Examiner*—Robert V. Hines
*Attorney, Agent, or Firm*—Martin B. Barancik

[57] ABSTRACT

4-Amino-4-cyclohexan-1-ols are formulated into pharmaceutical compositions for the relief of pain in mammals in need of said treatment.

15 Claims, No Drawings

COMPOUNDS, COMPOSITIONS AND METHOD OF USE

BRIEFF DESCRIPTION OF THE INVENTION

Novel 4-amino-4-cyclohexan-1-ols are active as analgetics. These compounds are formulated into pharmaceutical compositions for the relief of pain in mammals in need of said treatment.

DETAILED DESCRIPTION OF THE INVENTION

In accordance with this invention there are provided compounds of Formula I and hereafter referred to as Group A Formula I

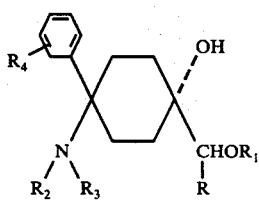

wherein R is hydrogen or alkyl of one to three carbon atoms, inclusive, $R_1$ is hydrogen or

wherein $R_5$ is alkyl of one to six carbon atoms, inclusive; $R_2$ and $R_3$ are the same or different and are alkyl of one to five carbon atoms, inclusive; and $R_4$ is hydrogen, meta or para halo, hydroxy or alkyl of one to three carbon atoms, inclusive, and physiologically acceptable acid addition salts thereof.

A further group of compounds, hereafter referred to as Group B, are the compounds of Group A wherein R is hydrogen; $R_1$ is hydrogen or

wherein $R_5$ is alkyl of one to three carbon atoms, inclusive; $R_2$ and $R_3$ are alkyl of one to three carbon atoms, inclusive; and $R_4$ is meta or para halo or hydroxy.

A still further group of compounds are those of Group B wherein $R_1$ is hydrogen and $R_2$ and $R_3$ are methyl.

Another group of compounds are those of Group B wherein $R_4$ is para, chloro, bromo or meta hydroxy.

Prefered compounds are those compounds wherein R and $R_1$ are hydrogen, $R_2$ and $r_3$ are methyl and $R_4$ is meta hydroxy or para bromo. Another preferred compound is the compound wherein R and $R_1$ are hydrogen, $R_2$ is n-butyl, $R_3$ is methyl and $R_4$ is meta hydroxy.

Another aspect of the invention is pharmaceutical compositions of each of the groups of compounds. A still further aspect of the invention is the method of using each of the pharmaceutical compositions for the utility of the invention.

As employed throughout this specification and claims, the phrase "alkyl of one to six carbon atoms, inclusive" means methyl, ethyl, n-propyl, n-butyl, n-pentyl, n-hexyl and isomers thereof. Illustrative examples of isomers are isopropyl, t-butyl, neopentyl, and 2,3-dimethylbutyl. Alkyl of a lower carbon atom limitation is to be interpreted in the same manner. "Halo" is intended to include fluoro, chloro, bromo and iodo. The term "physiologically acceptable acid addition salt" refers to an acid attached to the basic amino function of the molecule, thereby forming a compound which is essentially non-toxic to the host animal. Illustrative examples of suitable acid are hydrochloric, sulfuric, nitric, acetic, propionic, lauric, palmitic, cyclohexanesulfamic, p-toluenesulphonic and the like.

The compounds of the invention are readily prepared by chemical synthetic methods. A 4-oxocyclohexanone monoketal prepared by methods known in the art, see M. Haslanger and R. G. Lawton, *Synthetic Commun.*, 4,155 (1974), is reacted with an $NR_2R_3$ acid addition salt and an alkali metal cyanide to fform a 4-dialkylamino-4-cyanocyclohexanone ketal. The reaction between the ketal, amine acid addition salt and cyano proceeds readily and does not usually require heating. Room temperature and stirring are suitable. Standard recovery and purification methods are employed. Either potassium or sodium cyanide can be employed. With respect to the ketal, any alkylene ketal is suitable; however, an ethylene ketal prepared with an ethylene glycol in the presence of an acid catalyst such as p-toluenesulfonic acid and an organic solvent is preferred. The ketalization reaction is promoted by heating, preferably at the reflux temperature, and azeotropic removal of the water by-product.

The 4-dialkylamino-4-cyanocyclohexanone ketal is then reacted with a Grignard reagent of the type

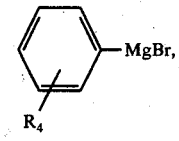

$R_4$ defined as above, in a Grignard reaction to form a 4-dialkylamino-4-phenylcyclohexanone ketal. When $R_4$ in the final product is to be hydroxy, the hydroxy function of the Grignard reagent is protected by a group which can be removed under mild conditions at a convenient place further along the synthetic pathway. An example of such a group is tetrahydropyranyl or benzyloxy. Such a group can be removed under mild hydrolytic conditions using aqueous acid, e.g., hydrochloric, acetic, and the like or by hydrogenolysis over a catalyst such as Pd/c.

This Grignard reaction occurs when the Grignard reagent and the ketal are heated, preferably to the reflux temperature in an organic solvent medium. A suitable organic solvent medium is tetrahydrofuran, preferably anhydrous. Heating periods are relative lengthy. Eighteen to 72 hours may be required, although fifteen to 24 hours is generally an adequate reaction time. The 4-dialkylamino-4-phenylcyclohexanone ketals are recovered in the usual manner by decomposition of the reaction mixture with a neutral aqueous medium, e.g., ammonium chloride. The organic layer is purified by standard techniques.

At this point in the synthetic pathway, the ketal is cleaved, thereby forming the substituted cyclohexanone, by contacting the ketal in an aqueous mineral acid such as hydrochloric acid in the presence of an organic solvent such as methanol. This contacting time is relatively lengthy; time periods of up to 48 hours may be necessary. During this reaction, the hydroxy protecting group, if present, will also be cleaved, leaving $R_4$ as hydroxy. Such cleavage can occur prior to the ketal conversion if desired.

The 4-dialkylamino-4-phenylcycloexhanone is then reacted with a Wittig reagent such as $O_3P=CHR$, R defined as above, thereby forming the 4-dialkylamino-4-phenylcyclohexane methylene compound. Standard Wittig reagents and conditions are employed.

The methylene compound is then oxidized with an oxidizing agent such as osmium tetroxide to form compounds of Formula I wherein $R_1$ is hydrogen. When using osmium tetroxide, a basic amine solvent is also employed. A further organic co-solvent can also be employed if desired. To obtain compounds of Formula I wherein $R_1$ is $R_5CO$, $R_5$ defined as above, as selective acylation is undertaken. A standard acylating such as an anhydride, for example acetic anhydride, is reacted with the glycol of Formula I at a low temperature, for example 0° to 35° C., for a period of time, e.g., 2–30 hours, followed by basic work-up, thereby forming compounds of formula I wherein $R_1$ is $R_5CO$.

The compounds of Formula I can occur in their cis and trans forms.

Illustrative examples of compounds of this invention are represented in Table I below.

Table I

[Structure shown: cyclohexane ring with $R_4$-phenyl, OH, N($R_2$)($R_3$), and CHOR$_1$ with R substituents]

| R | $R_1$ | $R_2$ | $R_3$ | $R_4$ |
|---|---|---|---|---|
| H | H | CH$_3$ | CH$_3$ | m-F |
| CH$_3$ | H | C$_2$H$_5$ | C$_5$H$_{11}$ | p-Cl |
| C$_2$H$_5$ | H | C$_3$H$_7$ | C$_4$H$_9$ | m-OH |
| C$_3$H$_7$ | H | i-C$_3$H$_7$ | CH$_3$ | p-CH$_3$ |
| i-C$_3$H$_7$ | H | t-C$_4$H$_9$ | C$_2$H$_5$ | m-C$_2$H$_5$ |
| C$_2$H$_5$ | H | C$_2$H$_5$ | C$_2$H$_5$ | p-Br |
| H | CH$_3$C(=O) | C$_3$H$_7$ | i-C$_3$H$_7$ | p-CH$_3$ |
| H | C$_2$H$_5$C(=O) | C$_4$H$_9$ | C$_4$H$_9$ | m-C$_3$H$_7$ |
| CH$_3$ | C$_3$H$_7$C(=O) | C$_5$H$_{11}$ | CH$_3$ | m-I |
| C$_3$H$_7$ | i-C$_4$H$_9$C(=O) | i-C$_5$H$_{11}$ | C$_2$H$_5$ | p-F |
| H | H | C$_4$H$_9$ | CH$_3$ | m-OH |
| H | CCH$_3$(=O) | CH$_3$ | CH$_3$ | p-Br |
| H | H | CH$_3$ | CH$_3$ | p-Br |
| H | H | CH$_3$ | CH$_3$ | H |
| H | CH$_3$C(=O) | C$_2$H$_5$ | CH$_3$ | H |
| CH$_3$ | C$_2$H$_5$C(=O) | i-C$_3$H$_7$ | i-C$_3$H$_7$ | H |
| C$_2$H$_5$ | H | C$_4$H$_9$ | C$_2$H$_5$ | H |
| C$_2$H$_5$ | i-C$_5$H$_{11}$C(=O) | t-C$_4$H$_9$ | CH$_3$ | m-Cl |
| i-C$_3$H$_7$ | H | C$_2$H$_5$ | C$_2$H$_5$ | p-OH |
| H | H | C$_3$H$_7$ | CH$_3$ | m-CH$_3$ |
| H | C$_6$H$_{13}$C(=O) | CH$_3$ | C$_2$H$_5$ | p-C$_2$H$_5$ |
| H | H | C$_4$H$_9$ | CH$_3$ | m-i-C$_3$H$_7$ |

Table I-continued

[Structure shown same as above]

| R | $R_1$ | $R_2$ | $R_3$ | $R_4$ |
|---|---|---|---|---|
| H | H | C$_2$H$_5$ | C$_2$H$_5$ | p-I |
| C$_3$H$_7$ | C$_2$H$_5$C(=O) | C$_5$H$_{11}$ | CH$_3$ | m-OH |
| CH$_3$ | H | i-C$_3$H$_7$ | CH$_3$ | p-OH |
| C$_2$H$_5$ | t-C$_4$H$_9$C(=O) | C$_4$H$_9$ | C$_2$H$_5$ | m-F |
| i-C$_3$H$_7$ | C$_3$H$_7$C(=O) | C$_3$H$_7$ | i-C$_3$H$_7$ | p-F |
| H | H | C$_2$H$_5$ | C$_2$H$_5$ | m-C$_2$H$_5$ |
| H | CH$_3$C(=O) | CH$_3$ | CH$_3$ | p-i-C$_3$H$_7$ |

TABLE II

Various acid addition salts of the free base compounds of Table I are prepared by adding the free base to the appropriate acid in an appropriate solvent, e.g., alcohol. For example, the hydrochloric, sulfuric, nitric, hydrobromic, acetic, propionic, maleic, pamoic and lauric acid addition salts of the compounds of Table I are prepared in this manner.

Following are specific examples of the compounds of this invention. These examples are not intended to limit but are presented to exemplify the scope of the invention. The compounds can be separated into their cis and trans forms.

EXAMPLE 1

Cis and trans
4-dimethylamino-4-(p-chlorophenyl)-1-hydroxymethyl-cyclohexan-1-ol Part A— Preparation of precursor cyclohexane-1,4-dione, ethylene monoketal A reaction mixture consisting of 10 g. (0.085 mole) 4-hydroxycyclohexanone, 4.75 ml. ethylene glycol, 0.20 g. p-toluenesulfonic acid, and 100 ml. benzene is heated at the reflux temperature in a reaction vessel fitted with a Dean and Stark trap for 2 hours. After the reaction mixture has cooled, it is washed first with water and then with brine. The benzene is then removed by evaporation under reduced pressure giving the intermediate 4-hydroxycyclohexanone ethylene monoketal as a viscous oil weighing 14.12 g.. The 4-hydroxycyclohexanone ethylene monoketal is dissolved in 100 ml. methylene chloride and added with stirring to a suspension consisting of 55.0 g. chromium trioxide (pre-dried for 24 hours under reduced pressure over phosphorous pentoxide), one liter dry methylene chloride, and 52.8 g. 3,5-dimethylpyrazole. After continued stirring for ten (10) minutes, this dark reaction mixture is poured onto a two-liter column of silica gel. When the reaction mixture has been completely adsorbed, the chromatogram is developed with a 1:1 mixture of ethyl acetate and technical hexane (Skellysolve B — a mixture of isomeric hexanes having a boiling range between 60° and 70° C.). The appropriate fractions as determined by TLC are collected and combined, after which the solvents are removed by evaporation under reduced pressure. The crystals thus obtained are recrystallized from technical hexane, and there is thus obtained 10.82 g. (91% yield) of the desired cyclohexane — 1,4-dione, ethylene monoketal having a melting point at 68° to 69° C. [The literature value is 71.5° to 72.5° C.]

Part B

Preparation of first intermediate 4-cyano-4-dimethylaminocyclohexanone, ethylene ketal A reaction mixture consisting of 3.0 g. (0.019 mole) of the cyclohexane-1,4-dione, ethylene monoketal prepared in Part A, above, 3.0 g. potassium cyanide, 4.5 g. dimethylamine hydrochloride, 3.0 ml. methanol, and 25 ml. saturated aqueous dimethylamine is stirred at 25° C. for 48 hours. The reaction mixture is then extracted successively with five 40 ml.-portions of diethyl ether. The ether extracts are combined and the ether is removed by evaporation under reduced pressure. The residue thus obtained is dissolved in methylene chloride. Some small amount of water present is separated, and the organic solvent portion is conserved for removal of the methylene chloride by evaporation under reduced pressure. The residual solid thus obtained is recrystallized from technical hexane to give 3.6 g. (78% yield) of the desired intermediate 4-cyano-4-dimethylaminocyclohexanone ethylene ketal having a melting point at 79° to 81° C.

Anal. Calcd. for $C_{11}H_{17}N_2O_2$: C, 62.83; H, 8.63; N, 13.33 Found: C, 62.92; H, 8.66; N, 13.58.

Part C

Preparation of 4-(p-chlorophenyl)-4-dimethylaminocyclohexanone, ethylene ketal hydrochloride To a Grignard reagent prepared from 2.73 g. of p-chlorobromobenzene, 0.35 g. magnesium and 30 ml. tetrahydrofuran (THF), is added 1.50 g. (0.071 mole) of 4-cyano-4-dimethylaminocyclohexanone ethylene ketal (prepared in Part B) in 40 ml. of THF. The reaction mixture is heated for three (3) days at the reflux temperature. It is then cooled, chilled in an ice bath and 20 ml. saturated ammonium chloride in benzene added. The organic phase is separated. It is washed initially with water and then with brine. Finally, the solvents are removed by evaporation under reduced pressure. The residue thus obtained is dissolved in diethyl ether and 4 N ethereal hydrogen chloride is added until precipitation is complete. The salt thus obtained is collected on a filter as a gummy material. It is suspended in methylene chloride and one N aqueous sodium hydroxide is added. The organic layer is separated and the methylene chloride is removed by evaporation under reduced pressure. The residue thus obtained is added onto a 200 ml. column of silica gel, the chromatogram is developed with methylene chloride containing 4% methanol and 20-ml. fractions are collected. The solvent is removed by evaporation under reduced pressure and the residue is dissolved in diethyl ether. The ether solution is treated with 4 N ethereal hydrogen chloride until precipitation of the desired 4-(p-chlorophenyl)-4-dimethylaminocyclohexanone ethylene ketal hydrochloride is complete. The precipitate is collected on a filter and crystallized from a mixture of methylene chloride and ethyl acetate to give 0.80 g. (34% yield) of pure 4-(p-chlorophenyl)-4-dimethylaminocyclohexanone ethylene ketal hydrochloride having a melting point at 252° to 254° C.

Part D

Preparation of 4-(p-chlorophenyl)-4-dimethylaminocyclohexanone

A reaction solution consisting of 4.52 g. (0.0136 mole) of 4-(p-chlorophenyl)-4-dimethylaminocyclohexanone, ethylene ketal hydrochloride (prepared in Part C above), 22.5 ml. 2.5 N hydrochloric acid, and 45 ml. methanol is set aside at 25° C. for 48 hours. The methanol medium is substantially removed by evaporation under reduced pressure to give a concentrate that is made strongly basic by additions of 50% aqueous sodium hydroxide. A precipitate forms which is collected on a filter and dissolved in diethyl ether. This ether solution is washed with brine to remove the residual water and the ether is then removed by evaporation under reduced pressure. The residue thus obtained is recrystallized from diethyl ether to give 2.30 g. (70% yield) of 4-(p-chlorophenyl)-4-dimethylaminocyclohexanone having a melting point at 108° to 111° C.

Anal. Found: C, 67.10; H, 7.36; N, 5.42.

Part E

4-Dimethylamino-4-(p-chlorophenyl)-1-exomethylene-cyclohexane hydrochloride

Butyl lithium (16.4 ml. of 1.68N solution in pentane) is added to a suspension of 8.75 g. of finely powdered methyltriphenylphosphonium bromide in 70 ml. tetrahydrofuran. Following 15 minutes stirring, there is added a solution of 3.0 g. (12 mmole) of the ketone prepared in Part D in 40 ml. tetrahydrofuran. At the end of 48 hours stirring at room temperature, the mixture is treated with 25 ml. saturated aqueous $NH_4Cl$ and benzene. The organic layer is separated, washed one with water and then extracted with 4 portions of 50 ml. each of 2.5N HCl. The acidic extracts are combined, made strongly basic with 50% NaOH and the precipitated gum extracted with $CHCl_3$. The organic extracts are combined, treated with an excess of 2.5N ethereal HCl and taken to dryness. The residual solid is recrystallized from $CH_2Cl_2$:EtOAc to give 3.25 g. (92%) of product, melting point 112°–116° C. A sample was further recrystallized to give material which melts at 115° C., resolidifies, then melts at 198°–202° C.

Anal. Found: C, 60.77; H, 7.44; N, 3.94.

Part F

Cis and trans 4-dimethylamino-4-(p-chlorophenyl)-1-hydroxymethyl-cyclohexan-1-ol A solution of the free base from 1.37 g. (5 mmole) of the amine hydrochloride, 0.76 g. N-methylmorpholine oxide and 20 mg. osmium tetroxide and 20 ml. tert butyl alcohol is stirred at room temperature for 7 hours. The bulk of the solvent is removed in vacuum. The residue is dissolved in benzene, the solution washed with water and brine and taken to dryness. The residue is chromatographed by high pressure liquid chromatography on a 1 × 48 inch silica gel column (1% ammonia, 15% MeOH in $CHCl_3$). There is obtained first 0.14 g. of starting olefin followed next by a glycol [0.60 g., melting point 140°–142° C., nmr δ3.65 (S,2,$CH_2OH$)] and finally the more polar glycol (0.49 g., melting point 95°–99° C., nmr δ3.85 (S,2,$CH_2OH$).

The less polar glycol is recrystallized from $CHCl_3$: Skellysolve B (a mixture of low boiling alkanes) to give 0.43 g. (29%) of product, melting point 142°–143° C.

Anal. Found: C, 62.62; H, 7.99; N, 4.78.

The more polar glycol is recrystallized from $CH_2Cl_2$: Skellysolve B to afford 0.33 g. (23%) of product, melting point 100°–104° C.

Anal. Found: C, 61.19; H, 8.10; N, 4.50.

EXAMPLE 2

1-Acetoxymethyl-4-dimethylamino-4-(p-chlorophenyl)cyclohexan-1-ol hydrochloride

A solution of 0.31 g. (1 mmole) of the more polar glycol of Example 1, 0.21 ml. acetic anhydride and 0.30 g. triethylamine in 10 ml. tetrahydrofuran is allowed to stand at room temperature for 6 hours. The bulk of the solvent is then removed in vacuum and the residue treated with ice. The mixture is then made basic and extracted with $CH_2Cl_2$. The gum which remains when the extract is taken to dryness is chromatographed on a preparative tlc plate (20% $MeOH:CH_2Cl_2$). The appropriate fraction is scraped off, eluted and converted to the hydrochloride salt. This is recrystallized from methylene chloride: ethyl acetate to afford 0.10 g. (24%) of product, melting point 220°–221° C.

Anal. Found: C, 56.25; H, 7.04; N, 3.97.

EXAMPLE 3

1-Acetoxymethyl-4-dimethylamino-4-(p-chlorophenyl)cyclohexan-1-ol hydrochloride

To an ice cooled solution of 0.97 g. (3.1 mmole) of the less polar glycol of Example 1 in 35 ml. tetrahydrofuran there is added 0.66 ml. acetic anhydride and 0.94 ml. triethylamine. Following 18 hours standing in the cold the bulk of the solvent is removed in vacuum. The residue is treated with ice and made basic with sodium bicarbonate. The precipitated gum is extracted with chloroform and this solution taken to dryness. The residual gum is converted to the hydrochloride salt and the salt recrystallized from MeOH:EtOAc. There is obtained 0.78 g. (70%) of product, melting point 235°–236° C.

Anal. Found: C, 55.97; H, 6.86; N, 3.60.

Preferred compounds other than the compound of Example 1 are the compounds of Formula I where R and $R_1$ are hydrogen, $R_2$ and $R_3$ are methyl and $R_4$ is meta hydroxy or para bromo. These compounds are readily prepared by the above procedures wherein the hydroxy group is protected as previously disclosed.

The compounds are administered orally, parenterally and rectally for systemic action.

The compositions of the present invention are presented for administration to humans and animals in unit dosage forms, such as tablets, capsules, pills, powders, granules, sterile parenteral solutions or suspensions, and oral solutions or suspensions, and oil-water emulsions containing suitable quantities of a compound of Formula I or its pharmacologically acceptable salts.

Pharmaceutical dosage unit forms are prepared in accordance with the subsequent general specific descriptions to provide from about 0.5 mg. to about 100 mg. of the essential active ingredient per dosage unit form (preferred 2-30 mg.).

Oral pharmaceutical dosage forms are either solid or liquid. The solid dosage forms are tablets, capsules, granules, and bulk powders. Types of oral tablets are, for example, compressed (including chewable and lozenge), tablet triturates, enteric-coated, sugar-coated, film-coated, and multiple compressed. Capsules are either hard or soft elastic gelatin. Granules and powders are either effervescent of non-effervescent.

Pharmaceutically acceptable substances utilized in compressed tablets are binders, lubricants, diluents, disintegrating agents, coloring agents, flavoring agents, flow inducing agents, and wetting agents. Tablet triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which usually four different layers of pharmaceutically acceptable substances have been applied. Film-coated tablets are compressed tablets which have been coated with a water soluble cellulose polymer. Multiple compressed tablets are compressed tablets made by more than one compression cycle utilizing the pharmaceutically acceptable substances previously mentioned. Coloring agents are utilized in the above dosage forms. Flavoring and sweetening agents are utilized in compressed tablets, tablet triturates, sugar coated, multiple compressed and chewable tablets. Flavoring and sweetening agents are especially useful in the formation of chewable tablets and lozenges.

Examples of binders include glucose solution (25-50%), acacia mucilage (10-20%), gelatin solution (10-20%), sucrose and starch paste. Lubricants include, for example, talc, starch, magnesium or calcium stearate, lycopodium and stearic acid. Diluents include, for example, lactose, sucrose, starch, kaolin, salt, mannitol, and dicalcium phosphate. Disintegrating agents include, for example, corn starch, potato starch, bentonite, methylcellulose, agar and carboxymethylcellulose. Coloring agents include, for example, any of the approved certified water-soluble FD and C dyes, mixtures thereof, and water insoluble FD and C dyes suspended on alumia hydrate. Sweetening agents include, for example, sucrose, lactose, mannitol, and artificial sweetening agents such as sodium cyclamate and saccharin, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monooleate, diethylene glycol monolaurate and polyoxyethylene lauryl ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets, include, for example, dextrin and gelatin. The second layer, an opaque zone, includes, for example, starch, talc, calcium carbonate, magnesium oxide and magnesium carbonate. The third layer, a translucent zone, includes, for example, sucrose. The fourth layer, a glaze, includes, for example, beeswax, carnauba wax, or a mixture of these waxes. Film coatings include, for example, hydroxyethylcellulose, sodium carboxymethylcellulose, polyethylene glycol 4000 and cellulose acetate phthalate.

Hard gelatin capsules, sizes 5 through 1000, are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastrointestinal tract, polyvinyl alcohol, ethyl cellulose and mixtures of beeswax, carnauba wax or bayberry wax with glyceryl monostearate.

Soft elastic gelatin capsules contain sufficient glycerin so that they are permanently flexible. Pharmaceutically acceptable liquid diluents used in soft elastic gelatin capsules are those which do not dissolve or harm the capsule and which are non-toxic, including, for example, corn oil, cottonseed oil, polysorbate 80, DMA and triacetin.

Pharmaceutically acceptable substances utilized in non-effervescent granules, for solution and/or suspension, include diluents, wetting agents, flavoring agents and coloring agents. Examples of diluents, wetting agents, flavoring agents and coloring agents include those previously exemplified.

Pharmaceutically acceptable substances utilized in effervescent granules and powders include organic acids, a source of carbon dioxide, diluents, wetting agents, flavoring agents and coloring agents.

Examples of organic acids include, for example, citric acid and tartaric acid. Sources of carbon dioxide include, for example, sodium bicarbonate and sodium carbonate. Examples of sweetening agents include, for example, sucrose, calcium cyclamate and saccharin. Examples of diluents, wetting agents and coloring agents include those previously exemplified.

Bulk powders have the compound of the Formula I uniformly dispersed throughout a pharmaceutically acceptable powdered carrier diluent. Examples of the diluent include those previously exemplified.

The individual oral solid pharmaceutical dosage forms, tablets and capsules, are packaged individually, unit-dose, or in quantity, multiple-dose containers, for example, bottles of 50, 100, 500, 1000, or 5000.

The amount of compound of the Formula I analog per dose unit is adjusted so that it provides the patient with an effective amount. The exact dose depends on the age, weight and condition of the patient or animal as is known in the art. For example, tablets and capsules are given in sufficient number and frequency to obtain the desired pharmacological effect.

The sustained release tablets and capsules provide an effective amount upon ingestion and continue to release a sufficient amount of the active material to keep the concentration at an effective level for increased periods of time, for example, 12 hours.

Non-effervescent granules and powders are packaged in predetermined amounts, such that when reconstituted with a specified quantity of an appropriate liquid vehicle, usually distilled water, a solution and/or suspension results providing a uniform concentration of the compound of the Formula I after shaking, if necessary. The concentration of the solution is such that a teaspoonful (5 ml.), a tablespoon (one-half ounce or 15 ml.) or a fraction or a multiple thereof will provide an effective amount to produce the desired pharmacological effect. The exact dose depends on the age, weight and condition of the patient or animal, as is known in the art.

Effervescent granules and powders are packaged either in unit-dose, for example, tin foil packets, or in bulk, for example, in 4 oz. and 8 oz. amounts, such that a specific amount, either a unit-dose or, for example, a teaspoonful, tablespoon or a fraction or a multiple thereof of bulk granules, when added to a specific amount of liquid vehicle, for example, water, yields a container of liquid dosage form to be ingested. The concentration of the active material in the granules is adjusted so that a specified amount when mixed with a specific amount of water yields an effective amount of the active material and produces the desired pharmacological effect. The exact amount of granules to be used depends on age, weight and condition of the patient as is known in the art.

Liquid oral dosage forms include, for example, aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water (o/w) or water-in-oil (w/o).

Elixirs are clear, sweetened, hydroalcoholic preparations. Pharmaceutically acceptable substances utilized in elixirs include, for example, solvents. Syrups are concentrated aqueous solutions of a sugar, for example, sucrose, and may contain a preservative. An emulsion is a two-phase system in which one liquid is dispersed in the form of small globules throughout another liquid. O/w emulsions are much preferred for oral administration over w/o emulsions. Pharmaceutically acceptable substances utilized in emulsions are non-aqueous liquids, emulsifying agent and preservatives. Suspensions utilize pharmaceutically acceptable suspending agents and preservatives. Pharmaceutically acceptable substances utilized in noneffervescent granules, to be reconstituted into a liquid oral dosage form, include, for example, diluents, sweeteners, and wetting agents. Pharmaceutically acceptable substances utilized in effervescent granules, to be reconstituted into a liquid oral dosage form, include, for example, organic acids and a source of carbon dioxide. Coloring and flavoring agents are utilized in all of the above dosage forms.

Solvents include, for example, glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include, for example, mineral oil and cottonseed oil. Examples of emulsifying agents include, for example, gelatin, acacia, tragacanth, bentonite, and surfactants such as polyoxyethylene sorbitan monooleate. Suspending agents include, for example, sodium carboxymethylcellulose, pectin, tragacanth, Veegum and acacia. Diluents include, for example, lactose and sucrose. Sweetening agents include, for example, sucrose, syrups, glycerin, and artificial sweetening agents such as sodium cyclamate and saccharin. Wetting agents include, for example, propylene glycol monostearate, sorbitan monooleate, diethylene glycol monolaurate and polyoxyethylene lauryl ether. Organic acids include, for example, citric and tartaric acid. Sources of carbon dioxide include, for example, sodium bicarbonate and sodium carbonate. Coloring agents include, for example, any of the approved, certified water soluble FD and C dyes, and mixtures thereof. Flavoring agents include, for example, natural flavors extracted from plants, such as fruits, and synthetic blends of compounds which produce a pleasant taste sensation.

The concentration of the compound of the Formula I throughout the solutions must be uniform. Upon shaking, the concentration of the compound of the Formula I throughout the emulsions and suspensions must be uniform.

The concentration of the compound of the Formula I is adjusted so that a teaspoonful (5 ml.), a tablespoonful (one-half ounce or 15 ml.) or a fraction or multiple thereof, will provide an effective amount to produce the desired pharmacological effect. The exact dose depends on the age, weight and condition of the patient or animal as is known in the art.

The liquid oral dosage forms may be packaged, for example, in unit-dose sizes of 5 ml. (teaspoonful), 10 ml., 15 ml. (tablespoon) and 30 ml. (one ounce), and multiple dose containers, including, for example, 2 oz., 3 oz., 4 oz., 6 oz., 8 oz., pint, quart, and gallon sizes.

Non-effervescent granules are packaged in predetermined amounts such that when reconstituted with a specified quantity of an appropriate liquid vehicle, usually distilled water, a solution and/or suspension results providing a uniform concentration of the compound of the Formula I after shaking, if necessary. The concentration of the solution is such that a teaspoonful (5 ml.), a tablespoonful (one-half ounce or 15 ml.) or a fraction or multiple thereof will provide an effective amount to produce the desired pharmacological effect. The exact dose depends on the age, weight, and condition of the patient or animal as is known in the art.

Effervescent granules are packaged either in unit-dose, for example, tin foil packets, or in bulk, for example, in 4 oz. and 8 oz. amounts such that a specific amount, either a unit-dose of for example, a teaspoonful, a tablespoonful or a fraction or multiple thereof of bulk granules when added to a specific amount of liquid vehicle, for example, water, yields a container of liquid dosage form to be ingested. The concentration of the compound of the Formula I in the granules is adjusted so that a specified amount when mixed with a specific amount of water yields an effective amount of the active material to produce the desired pharmacological effect. The exact amount of granules to be used depends on age, weight and condition of the patient as is known in the art.

Parenteral administration includes intravenous, subcutaneous, intramuscular, and the like.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Pharmaceutically acceptable solutions utilized in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutical necessities.

Examples of aqueous vehicles include Sodium Chloride Injection, Ringers Injection, Isotonic (5 percent) Dextrose Injection, Sterile Water for Injection, Dextrose and Sodium Chloride injection and Lactated Ringers Injection. Nonaqueous parenteral vehicles include fixed oils of vegetable origin, for example, cottonseed oil, corn oil, sesame oil and peanut oil. Antimicrobial agents in bacteriostatic or fungistatic concentrations must be added to parenteral preparations packaged in multiple-dose containers (vial) which include phenol or cresols, mercurials, benzyl alcohol, chlorobutanol, methyl and propy p-hydroxybenzoic acid esters, thimerosal, benzalknoium chloride and benzethonium chloride. Isotonic agents include, for example, sodium chloride and dextrose. Buffers include, for example, phosphate and citrate. Antioxidants include, for example, sodium bisulfite. Local anesthetics include, for example, procaine hydrochloride. Suspending and dispersing agents include, for example, sodium carboxymethylcellulose, hydroxypropyl methylcellulose and polyvinylpyrrolidone. Emulsifying agents include, for example, Polysorbate 80 (Tween 80). A sequestering or chelating agent of metal ions include, for example, EDTA (ethylenediaminetetraacetic acid). Pharmaceutical necessities include, for example, ethyl alcohol, polyethylene glycol and propylene glycol for water miscible vehicles and sodium hydroxide, hydrochloric acid, citric acid or lactic acid for pH adjustment.

The concentration of the pharmaceutically active ingredient is adjusted so that an injection, for example, 0.5 ml., 1.0 ml., 2.0 ml., and 5.0 ml. or an intraarterial or intravenous infusion, for example, 0.5 ml./min., 1.0 ml./min., 1.5 ml./min., and 2.0 ml./min. provides an effective amount to produce the desired pharmacological effect. The exact dose depends on the age, weight and condition of the patient or animal as is known in the art.

The unit-dose parenteral preparations are packaged, for example, in an ampul or a syringe with a needle. The multiple-dose package, for example, is a vial.

All preparations for parenteral administration must be sterile, as is known and practiced in the art.

Illustratively, intravenous or intraarterial infusion of a sterile aqueous solution containing an active material is an effective mode of administration. Another embodiment is a sterile aqueous or oily solution or suspension containing an active material injected as necessary to produce the desired pharmacological effect.

Pharmaceutical dosage forms for rectal administration are rectal suppositories, capsules, tablets for systemic effect.

Rectal suppositories as used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases or vehicles include, for example, cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include, for example, spermaceti and wax. Rectal suppositories may be prepared either by the compressed method or by molding. The usual weight of a rectal suppository is about 2.0 g.

Tablets and capsules for rectal administration are manufactured utilizing the same pharmaceutically acceptable substance and by the same methods as for formulations for oral administration.

Rectal suppositories, tablets or capsules are packaged either individually, in unit-dose, or in quantity, multiple dose, for example, 2, 6, or 12.

The pharmaceutically therapeutically active compounds of the Formula I are administered orally, parenterally or rectally in unit-dosage forms or multiple-dosage forms. Unit-dose forms as used in the specification and claims refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampuls and syringes (parenteral), individually packaged tablet or capsule (oral-solid) or individually packaged teaspoonful or tablespoonful (oral-liquid). Unit-dose forms may be administered in fractions or multiples thereof. A multiple-dose form is a plurality of identical unit-dosage forms packaged in a single container to be administered in segregated unit-dose form. Examples of multiple-dose forms include vials (parenteral), bottles of tablets or capsules (oral-solid) or bottles of pints or gallons (oral-liquid). Hence, multiple dose form is a multiple of unit-doses which are not segregated in packaging. The specifications for the unit-dosage form and the multiple dosage form are dictated by and directly dependent on (a) the unique characteristics of the therapeutically active compound and the particular therapeutic effect to be achieved and (b) the limitations inherent in the art of compounding such a therapeutically active compound for therapeutic or prophylactic.

In addition to the administration of a compound of Formula I as the principal active ingredient of composition for the treatment of the conditions described herein, the said compound can be included with other types of compounds to obtain advantageous combinations of properties. Such combinations include a compound of Formula I with other analgesics such as aspirin, phenacetin acetaminophen, propoxyphene, pentazocine, codeine, meperidine, oxycodone, mefenamic acid, and ibuprofen; muscle relaxants such as methocarbamol, orphenadrine, carisoprodol, meprobamate, chlorophenes in carbamate, diazepam, chlordiazepoxide, and chlorzoxazone; analeptics such as caffeine, methylphenidate and pentylenetatrazol; corticosteroids such as methylprednisolone, prednisone, prednisolone and dexamethasone; antihistamines such as chlorpheniramine, cyproheptadine, promethazine and pyrilamine.

The compounds of the Formula I have analgetic activity and can be used for the relief of pain without loss of consciousness. The compounds can be used to treat the pain of headache, muscle spasm, arthritis and other musculoskeletal conditions, e.g., bursitis, relieve mild to moderate postoperative and postpartum pain; dysmenorrhea and pain of traumatic origin. Additionally, the compounds of Formula I can be administered for the treatment of severe pain, e.g., pain associated with adenocarcinoma, amputation of a limb, and third degree burns over a major portion of the body in animals and humans.

The dosage of the compound of the Formula I for analgetic purposes is from about 0.01 to about 1.5 mg./kg. body weight of the patient, preferably from about 0.04 to about 0.4 mg./kg. The compounds of the Formula I are conveniently prepared in 5, 10, 25, 50, 75 and 100 mg. dosage units for administration for 1 to 4 times a day.

EXAMPLE 4

Capsules

One thousand two-piece hard gelatin capsules for oral use, each containing 5 mg. of 4-dimethylamino-4-(p-chlorophenyl)-1-hydroxymethylcyclohexan-1-ol are prepared from the following types and amounts of materials:

| | |
|---|---|
| 4-Dimethylamino-4-(p-chlorophenyl)-1-hydroxymethylcyclohexan-1-ol | 5 g. |
| Lactose | 150 g. |
| Corn Starch | 25 g. |
| Talc | 20 g. |
| Magnesium stearate | 2 g. |

The materials are thoroughly mixed and then encapsulated in the usual manner.

The foregoing capsules are useful for the treatment of headache in adult humans by the oral administration of one capsule every 4 hours.

Using the procedure above, capsules are similarly prepared containing 4-dimethylamino-4-(p-chlorophenyl)-1-hydroxymethylcyclohexan-1-ol in 10, 15, 30, 50 and 100 mg. amounts by substituting 10, 15, 30, 50 and 100 g. of 4-dimethylamino-4-(p-chlorophenyl)-1-hydroxymethylcyclohexan-1-ol for the 5 g. used above.

EXAMPLE 5

Capsules

One thousand two-piece hard gelatin capsules for oral use, each containing 25 mg. of 4-dimethylamino-4-(p-chlorophenyl)-1-hydroxymethylcyclohexan-1-ol and 325 mg. of aspirin, are prepared from the following types and amounts of ingredients:

| | |
|---|---|
| 4-Dimethylamino-4-(p-chlorophenyl)-1-hydroxymethylcyclohexan-1-ol | 25 g. |
| Aspirin | 325 g. |
| Talc | 35 g. |
| Magnesium stearate | 2 g. |

The ingredients are thoroughly mixed and then encapsulated in the usual manner.

The foregoing capsules are useful for the treatment of headache in adult humans by the oral administration of 1 capsule every 6 hours.

EXAMPLE 6

Tablets

One thousand tablets for oral use, each containing 15 mg. of 4-dimethylamino-4-(p-chlorophenyl)-1-hydroxymethylcyclohexan-1-ol are prepared from the following types and amounts of materials:

| | |
|---|---|
| 4-Dimethylamino-4-(p-chlorophenyl)-1-hydroxymethylcyclohexan-1-ol | 15 g. |
| Lactose | 125 g. |
| Corn Starch | 65 g. |
| Magnesium stearate | 2.5 g. |
| Light liquid petrolatum | 3 g. |

The ingredients are thoroughly mixed and slugged. The slugs are broken down by forcing through a number sixteen screen. The resulting granules are then compressed into tablets, each tablet containing 15 mg. of 4-dimethylamino-4-(p-chlorophenyl)-1-hydroxymethyl-cyclohexan-1-ol.

The foregoing tablets are useful for treatment of arthritic pain in adult humans by oral administration of one tablet every 4 hours.

EXAMPLE 7

Tablets

One thousand oral tablets, each containing 10 mg. of 4-dimethylamino-4-(p-chlorophenyl)-1-hydroxymethyl-cyclohexan-1-ol and a total of 400 mg. of chlorphenesin carbamate are prepared from the following types and amounts of materials:

| | |
|---|---|
| 4-Dimethylamino-4-(p-chlorophenyl)-1-hydroxymethylcyclohexan-1-ol | 10 g. |
| Chlorphenes in carbamate | 400 g. |
| Lactose | 50 g. |
| Corn Starch | 50 g. |
| Calcium stearate | 2.5 g. |
| Light liquid petrolatum | 5 g. |

The ingredients are thoroughly mixed and slugged. The slugs are broken down by forcing through a number sixteen screen. The resulting granules are then compressed into tablets, each containing 10 mg. of 4-dimethylamino-4-(p-chlorophenyl)-1-hydroxymethylcyclohexan-1-ol and 400 mg. of chlorphenesin carbamate.

The foregoing tablets are useful for treatment of low back pain by the oral administration of one tablet every 6 hours.

Example 8

Oral Syrup

One thousand ml. of an aqueous suspension for oral use, containing in each 5 ml. dose 30 mg. of 4-dimethylamino-4-(p-chlorophenyl)-1-hydroxymethylcyclohexan-1-ol is prepared from the following types and amounts of ingredients:

| | |
|---|---|
| 4-Dimethylamino-4-(p-chlorophenyl)-1-hydroxymethylcyclohexan-1-ol | 6 g. |
| Citric acid | 2 g. |
| Benzoic acid | 1 g. |
| Sucrose | 700 g. |
| Tragacanth | 5 g. |
| Lemon oil | 2 ml. |
| Deionized water q.s. | 1,000 ml. |

The citric acid, benzoic acid, sucrose, tragacanth, and lemon oil are dispersed in sufficient water to make 850 ml. of solution. The 4-dimethylamino-4-(p-chlorophenyl)-1-hydroxymethylcyclohexan-1-ol is stirred into the syrup until uniformly distributed. Sufficient water is added to make 1,000 ml.

The composition so prepared is useful in the treatment of headache in adult humans at a dose of 1 teaspoonful 4 times a day.

Example 9

Parenteral solution

A sterile aqueous solution for intramuscular use, containing in one ml. 10 mg. of 4-dimethylamino-4-(p-chlorophenyl)-1-hydroxymethylcyclohexan-1-ol is prepared from the following types and amounts of materials:

| | |
|---|---|
| 4-Dimethylamino-4-(p-chlorophenyl)-1-hydroxymethylcyclohexan-1-ol | 10 g. |
| Lidocaine hydrochloride | 4 g. |
| Methylparaben | 2.5 g. |
| Polyparaben | 0.17 g. |
| Water for injection q.s. | 1000 ml. |

The ingredients are dissolved in the water and the solution sterilized by filtration. The sterile solution is filled into vials and the vials sealed.

EXAMPLE 10

Suppository, rectal

One thousand suppositories, each weighing 2.5 g. and containing 30 mg. of 4-dimethylamino-4-(p-chlorophenyl)-1-hydroxymethylcyclohexan-1-ol are prepared from the following types and amounts of ingredients:

| | |
|---|---|
| 4-Dimethylamino-4-(p-chlorophenyl)-1-hydroxymethylcyclohexan-1-ol | 30 g. |
| Propylene glycol | 162.5 g. |
| Polyethylene glycol 4000 q.s. | 2500 g. |

The 4-dimethylamino-4-(p-chlorophenyl)-1-hydroxymethylcyclohexan-1-ol is added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The suppositories are useful in the treatment of headache by the insertion rectally of one suppository every 6 hours.

EXAMPLE 11

In a manner similar to Examples 4–10, the compounds of Examples 2, 3 and Table I are formulated into pharmaceutical compositions and used for analgetic purposes as in Examples 4–10.

I claim:

1. A compound of the formula

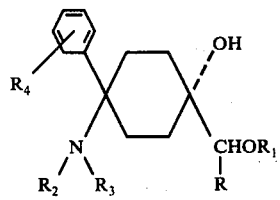

wherein R is hydrogen or alkyl of one to three carbon atoms, inclusive, $R_1$ is hydrogen $R_2$ and $R_3$ are the same or different and are alkyl of one to five carbon atoms, inclusive; and $R_4$ is hydrogen, meta or para halo, hydroxy or alkyl of one to three carbon atoms, inclusive, and physiologically acceptable acid addition salts thereof.

2. A compound in accordance with claim 1 wherein R is hydrogen; $R_2$ and $R_3$ are alkyl of one to three carbon atoms, inclusive; and $R_4$ is meta or para halo or hydroxy.

3. A compound in accordance with claim 2 wherein $R_2$ and $R_3$ are methyl.

4. A compound in accordance with claim 2 wherein $R_4$ is para bromo or meta hydroxy.

5. A compound in accordance with claim 1 wherein R is hydrogen, $R_2$ and $R_3$ are methyl, and $R_4$ is meta hydroxy or para bromo.

6. A compound in accordance with claim 1 wherein R is hydrogen, $R_2$ is n-butyl, $R_3$ is methyl and $R_4$ is meta hydroxy.

7. A pharmaceutical composition which comprises an analgetic effective amount of a compound of the formula

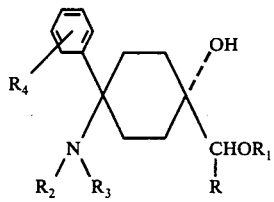

wherein R is hydrogen or alkyl of one to three carbon atoms, inclusive, $R_1$ is hydrogen, $R_2$ and $R_3$ are the same or different and are alkyl of one to five carbon atoms, inclusive; and $R_4$ is hydrogen, meta or para halo, hydroxy or alkyl of one to three carbon atoms, inclusive, and physiologically acceptable acid addition salts thereof, in association with a pharmaceutical carrier.

8. A composition in accordance with claim 7 wherein R is hydrogen.

9. A composition in accordance with claim 8 wherein $R_2$ and $R_3$ are methyl and $R_4$ is meta hydroxy or para bromo.

10. A composition in accordance with claim 8 wherein $R_2$ and $R_3$ are methyl and $R_4$ is para chloro.

11. A method for inducing analgesia in mammals in need of such treatment which comprises administering to said mammal an analgetically effective amount of a compound of the formula

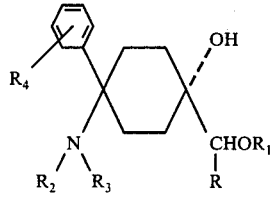

wherein R is hydrogen or alkyl of one to three carbon atoms, inclusive, $R_1$ is hydrogen, $R_2$ and $R_3$ are the same or different and are alkyl of one to five carbon atoms, inclusive; and $R_4$ is hydrogen, meta or para halo, hydroxy or alkyl of one to three carbon atoms, inclusive, and physiologically acceptable acid addition salts thereof.

12. A method in accordance with claim 11 wherein R is hydrogen.

13. A method in accordance with claim 12 wherein $R_2$ and $R_3$ are methyl and $R_4$ is meta hydroxy or para bromo.

14. A method in accordance with claim 12 wherein $R_2$ and $R_3$ are methyl and $R_4$ is para chloro.

15. A compound in accordance with claim 3 wherein $R_4$ is para chloro.

* * * * *

UNITED STATES PATENT OFFICE
CERTIFICATE OF CORRECTION

Patent No. 4,115,589             Dated September 19, 1978

Inventor(s) Daniel Lednicer

It is certified that error appears in the above-identified patent and that said Letters Patent are hereby corrected as shown below:

Column 1, line 55: "$R_2$ and $r_3$" should read -- $R_2$ and $R_3$ --
Column 3, line 6:  "phenylcycloexhanone" should read -- phenylcyclohexanone --
Column 3, line 7:  "$O_3P=CHR$," should read -- $\phi_3P=CHR$, --
Column 5, line 32: "$M_2O_2$:" should read -- $N_2O_2$: --

Signed and Sealed this

Eleventh Day of December 1979

[SEAL]

Attest:

SIDNEY A. DIAMOND

Attesting Officer

Commissioner of Patents and Trademarks